United States Patent
Fritchie et al.

(10) Patent No.: US 7,932,826 B2
(45) Date of Patent: Apr. 26, 2011

(54) SYSTEM FOR TRACKING THE LOCATION OF COMPONENTS, ASSEMBLIES, AND SUBASSEMBLIES IN AN AUTOMATED DIAGNOSTIC ANALYZER

(75) Inventors: Patrick P. Fritchie, Southlake, TX (US); Oscar F. Schwartz, Arlington, TX (US); Renee A. Lopez, Grand Prairie, TX (US)

(73) Assignee: Abbott Laboratories Inc., Abbott Park, IL (US)

( * ) Notice: Subject to any disclaimer, the term of this patent is extended or adjusted under 35 U.S.C. 154(b) by 246 days.

(21) Appl. No.: 12/137,638

(22) Filed: Jun. 12, 2008

(65) Prior Publication Data

US 2009/0309726 A1 Dec. 17, 2009

(51) Int. Cl.
*G08B 13/14* (2006.01)
(52) U.S. Cl. ............. 340/572.1; 340/572.4; 340/572.8
(58) Field of Classification Search .......... 340/572.1, 340/572.4, 539.1, 539.11, 573.1, 10.1, 10.42, 340/572.8, 539.12, 539.13, 10.4; 235/375, 235/376, 385; 422/64
See application file for complete search history.

(56) References Cited

U.S. PATENT DOCUMENTS

| | | | | |
|---|---|---|---|---|
| 7,098,793 B2 * | 8/2006 | Chung | ............. | 340/572.1 |
| 7,158,030 B2 * | 1/2007 | Chung | ............. | 340/572.1 |
| 7,382,255 B2 * | 6/2008 | Chung | ............. | 340/572.1 |
| 7,518,502 B2 * | 4/2009 | Austin et al. | ............. | 340/539.1 |
| 7,670,553 B2 * | 3/2010 | Babson | ............. | 422/64 |
| 2007/0018810 A1 | 1/2007 | Smythe et al. | | |
| 2008/0030345 A1 | 2/2008 | Austin et al. | | |

FOREIGN PATENT DOCUMENTS

DE 102005028476 A1 12/2006

OTHER PUBLICATIONS

The PCT International Search Report, Date of mailing Oct. 7, 2009.

(Continued)

*Primary Examiner* — Van T. Trieu
(74) *Attorney, Agent, or Firm* — David L. Weinstein (57) ABSTRACT

A system and method for the tracking of medical instrument, components, assemblies, and sub-assemblies thereof, and maintenance information relating to the foregoing. According to the system, radio frequency identification tags are attached to or affixed on the medical instrument itself for the purpose of locating, identifying, monitoring, tracking the medical instrument and updating the maintenance and replacement activities relating to the medical instrument. In addition, radio frequency identification tags are attached to or affixed on the components, the assemblies, and the sub-assemblies, of the medical instrument in order to locate, identify, monitor, track the components, the assemblies, and the sub-assemblies and update the maintenance and replacement activities relating to these components, assemblies, and sub-assemblies. The medical instrument itself can have a radio frequency identification tag; each major component of the automated diagnostic instrument can have a radio frequency identification tag; each minor component of the automated diagnostic instrument can have a radio frequency identification tag on the container in which it is packaged. A master radio frequency identification tag correlated with a database is needed in order to collect information relating to all of the radio frequency identification tags associated with the medical instrument.

31 Claims, 5 Drawing Sheets

OTHER PUBLICATIONS

Radio Frequency Identification (RFID). White Paper [online]. Accenture, 2001 [retrieved on May 23, 2008]. Retrieved from the Internet: <URL: http://www.accenture.com/NR/rdonlyres/D27DDAE-9-CAB2-43B5-B6F2-27BD4F22EC1C10/rfidwhitepaperenov01.pdf>, pp. 1-6, 13-19, 21, 23, 31-46.

Alien Technology, EPCglobal Class 1 Gen 2 RFID Specification. White Paper [online], 2005 [retrieved on Jun. 11, 2008]. Retrieved from the Internet: <URL: http://www.alientechnology.com/docs/AT_wp_EPCGlobal_WEB.pdf>, pp. 1-7.

Technologies: RFID/RFID Glossary. Brochure [online]. Association for Automatic Identification and Mobility [retrieved on May 23, 2008]. Retrieved from the Internet: <URL: http://www.aimglobal.org/technologies/rfid/rfid_Glossary.asp>.

ChannelWeb: Tools and information for the solution provider community. [online], [retrieved on Jun. 11, 2008]. Retrieved from the Internet: <URL: http://www.crn.com/encyclopedia/shared/printerFriendlySrc.jhtml?term=client/server>.

ChannelWeb: Tools and information for the solution provider community. [online], [retrieved on Jun. 11, 2008]. Retrieved from the Internet: <URL: http://www.crn.com/encyclopedia/shared/printerFriendlySrc.jhtml?term=file server>.

ChannelWeb: Tools and information for the solution provider community. [online], [retrieved on Jun. 11, 2008]. Retrieved from the Internet: <URL: http://www.crn.com/encyclopedia/shared/printerFriendlySrc.jhtml?term= databaseserver>.

ChannetWeb: Tools and information for the solution provider community. [online], [retrieved on Feb. 26, 2009]. Retrieved from the Internet: <URL: http://www.crn.com/encyclopedia/shared/printerFriendlySrc.jhtml?term=application server>.

Chaudhry, N., Thompson, D., and Thompson, C., RFID Technical Tutorial and Threat Modeling Version 1.0 [online], Dec. 8, 2005 [retrieved on Jun. 9, 2008]. Retrieved from the Internet: <URL: http://www.csce.uark.edu/~drt/presentations/rfid-tutorial-threats-051201.pdf>, pp. 1-39.

Crow, K., Configuration Management and Engineering Change Control [online], DRM Associates, 2002 [retrieved on Jun. 4, 2008]. Retrieved from the Internet: <URL: http://www.npd-solutions.com/configmgt.html>.

ID Technology. What is RFID & How Will it Impact My Business? [online], [retrieved on Jun. 9, 2008]. Retrieved from the Internet: <ULR: http://www.idtechnology.com/images/whitepapers/idtechnology-what-is-rfid.pdf>, pp. 1-11.

MF1ICS50 Functional specification, Rev. 5.3-Jan. 29, 2008, Document identifier: 001053, NXP B.V., pp. 1-19.

What is Wi-Fi?—A Word Definition From the Webopedia Computer Dictionary [online], [retrieved on Jun. 20, 2008]. Retrieved from the Internet: <URL: http://www.webopedia.com/TERM/W/Wi_Fi.html>.

What is 802.11—A Word Definition From the Webopedia Computer Dictionary [online], [retrieved on Jun. 10, 2008]. Retrieved from the Internet <URL: http://www.webopedia.com/TERM/8/802_11.html>.

Wi-Fi—Wikipedia, the free encyclopedia [online], [retrieved on Jun. 4, 2008]. Retrieved from the Internet: <URL: http://en.wikipedia.org/wiki/WiFi>.

Frequently Asked Questions About RFID Technology. Brochure [online]. Zebra Technologies, 2004 [retrieved on May 23, 2008]. Retrieved from the Internet: <URL: http://www.zebra.com/id/zebra/na/en/index/rfid/faqs.html>, pp. 1-21.

* cited by examiner

SYSTEM FOR TRACKING THE LOCATION OF COMPONENTS, ASSEMBLIES, AND SUBASSEMBLIES IN AN AUTOMATED DIAGNOSTIC ANALYZER

BACKGROUND OF THE INVENTION

1. Field of the Invention

This invention relates to tracking systems, more particularly, tracking systems for determining the location of components, assemblies, and sub-assemblies in medical instruments.

2. Discussion of the Art

Radio frequency identification (RFID) technology is an identification technology, which is capable of being automated, in which data are written to and data are read from tags that contain a microchip and an antenna by means of radio frequency signals. Radio frequency identification technology allows an active transmitter to selectively interrogate radio frequency identification tags attached to items of interest and capture the data transmitted from these radio frequency identification tags.

There are several methods for storing identification information in radio frequency identification systems, but the most common method involves storing a serial number that identifies a person or object, and other information, if desired, on a microchip, which is attached to an antenna. The microchip and the antenna together are referred to as a radio frequency identification transponder or a radio frequency identification tag. The antenna enables the microchip to transmit the identification information to a reader. The reader converts the radio waves transmitted from the radio frequency identification tag into digital information that can then be further transmitted to computers, which can use the information for various purposes.

Radio frequency identification tags can be provided in various shapes and sizes, can respond to various frequencies, and can be of various types. The shape(s) and the size(s) of a radio frequency identification tag(s) are generally a function of the radio frequency selected and the desired range, i.e., the distance between the radio frequency identification tag and the transmitter.

Radio waves behave differently at different frequencies; consequently, the appropriate frequency for a radio frequency identification tag must be selected for a given application. The available area of an object upon which the radio frequency identification tag can be attached or affixed is another factor that must be accounted for in the balancing of parameters necessary to determine a configuration. Frequencies for radio frequency identification tag are classified into three main categories: low frequency, around 125 KHz, high frequency, around 13.56 MHz, and ultra-high frequency, or UHF, around 860-960 MHz. Microwave frequency, around 2.45 GHz, can also be used in some applications. Radio frequency identification tags that utilize low frequency radio waves use less power, and, consequently, are more suitable for use for penetrating non-metallic substances than are radio frequency identification tags that utilize ultra-high frequency radio waves. Radio frequency identification tags that utilize low frequency radio waves are preferred for scanning objects having a high content of water, such as fruit, but their reading range is limited to less than a foot (0.33 meter). Radio frequency identification tags that utilize high frequency radio waves are useful for objects made of metal, and they can function well in the vicinity of objects having a high content of water. Radio frequency identification tags that utilize high frequency radio waves have a maximum reading range of about three feet (1 meter). Radio frequency identification tags that utilize ultra-high frequency radio waves typically provide greater range and can transfer data faster than can radio frequency identification tags that utilize low frequency radio waves or radio frequency identification tags that utilize high frequency radio waves. However, radio frequency identification tags that utilize ultra-high frequency radio waves require more power than do radio frequency identification tags that utilize low frequency radio waves and are less likely to pass through materials such as liquids and metals. Therefore, radio frequency identification tags that utilize ultra-high frequency radio waves generally require a clear path between the radio frequency identification tag and the reader. Radio frequency identification tags that utilize ultra-high frequency radio waves may be more useful for scanning labels on boxes of goods as they pass through a dock door into a warehouse than they would be for reading radio frequency identification tags that require a shorter read distance and a slower speed for reading, such as, for example, radio frequency identification tags that are used for controlled access to a building.

There are three types of radio frequency identification tags: passive, active, and semi-passive. Passive radio frequency identification tags are battery-free data-carrying devices that react to a specific reader produced inductively coupled or radiated electromagnetic field, by delivering a data modulated radio frequency response. Passive radio frequency identification tags draw power from the reader, which emits electromagnetic waves that induce a current in the antenna of the radio frequency identification tag. Active radio frequency identification tags are radio frequency identification tags that have a transmitter to send back information, rather than reflecting back a signal from the reader, as the passive radio frequency identification tag does. Active radio frequency identification tags have their own power source (typically a long-life battery). The power source is used to provide power to the circuitry of the microchip and to broadcast a signal to a reader. Such activity is analogous to the manner in which a cellular telephone transmits signals to a base station. Semi-passive radio frequency identification tags are radio frequency identification tags having batteries, but they communicate using the same backscatter technique as do passive radio frequency identification tags. They use the battery to provide power to run the circuitry of a microchip and sometimes an onboard sensor. They have a longer read range than a regular passive radio frequency identification tag because all of the energy gathered from the reader can be reflected back to the reader. Active and semi-passive radio frequency identification tags are useful for tracking goods of high value that need to be scanned over long ranges, such as railway cars on a track. However, active and semi-passive radio frequency identification tags are more expensive than are passive radio frequency identification tags, thereby making their cost too expensive for objects having a low value. However, future developments are expected to bring about a reduction in the cost of active radio frequency identification tags. Users often prefer passive radio frequency identification tags that utilize ultra-high frequency radio waves, which cost less than 40 U.S. cents per tag when ordered in volumes of one million tags or more. The range for reading passive frequency radio frequency identification tags that utilize ultra-high frequency radio waves is not as great as that of active radio frequency identification tags, e.g., less than 20 feet as compared with 100 feet or more for active radio frequency identification tags, but they are far less expensive than are active radio frequency identification tags and can be disposed of with the packaging for the object.

Most manufacturers of radio frequency identification tags do not quote prices, because pricing is based on volume, the memory capacity of the radio frequency identification tag, and the packaging of the radio frequency identification tag, e.g., whether the radio frequency identification tag is encased in plastic or embedded in a label. A typical cost for a 96-bit Electronic Product Code radio frequency identification tag ranges from about 20 to about 40 U.S. cents. If the radio frequency identification tag is embedded in a thermally transferred label onto which a bar code can be imprinted, the price rises to 40 U.S. cents, and even higher. The cost of a low frequency transponder encapsulated in glass is about $3.50, and the cost of a low frequency transponder in a plastic card or key fob is about $4.00 and can often be higher. The cost of high frequency transponders ranges from about $2.50 (in a card) to about $6.00 or more (for a key fob or other special embodiment).

The Department of Defense has employed radio frequency identification technology since the early 1990s to manage its complex supply chains around the world. There have been numerous developments in the capability of the technology to support this effort and further developments are expected as global standards in transmitter/receiver technology and data synchronization gain widespread acceptance. Transmitter and receiver frequency standards ensure that radio frequency identification tags and readers can operate in any electronic environment around the world. The International Organization for Standardization (ISO) is developing standards for tracking goods in a supply chain by means of high frequency radio frequency identification tags (ISO 18000-3) and ultra-high frequency tags (ISO 18000-6).

The Electronic Product Code (EPC) is a family of coding schemes that were created as the eventual successor to the bar code. The EPC was created as a low-cost method for tracking goods by means of radio frequency identification technology. The EPC is a serial, created by the Auto-ID Center, which will complement bar codes. The EPC has digits to identify the manufacturer, product category, and the individual item. The EPC system is currently managed by EPCglobal, which is a joint venture between GS1 and GS1 US. EPCglobal is an organization set up to achieve world-wide adoption and standardization of the Electronic Product Code technology in an ethical and responsible way. EPCglobal has its own standardization process, which was used to create bar code standards. EPCglobal intends to submit EPC protocols to ISO so that these protocols can become international standards. The following table (TABLE 1) lists radio frequency identification tag categories as defined by standards established by EPCglobal:

TABLE 1

| Parameter | Class 0 | Class 1 | Class 1 Generation 2 |
|---|---|---|---|
| Frequency | All | All | All |
| Read Rate | U.S.: 800 tags/second EU: 200 tags/second | U.S.: 200 tags/second EU: 50 tags/second | U.S.: 1700 tags/second EU: 600 tags/second |
| Rewriteability | Read Only | Write Once | Fully Rewritable |
| Privacy | 24-bit password | 8-bit password | 32-bit password (Concealed Mode) |
| Security | Reader broadcasts the identification number of the radio frequency identification tag, i.e., the signal can be received by anyone. | Reader broadcasts the identification number of the radio frequency identification tag, i.e., the signal can be received by anyone. | Reader does not transmit the identification number of the radio frequency identification tag. Authentication Encryption is required, i.e., confidential authorization must be used to obtain access to information. |
| Regulatory Compliance | North America | North America | World-wide |
| Multi-Reader Environment | Transmissions from the reader are separated physically, i.e., a physical separation reduces signal crossover and interference. | Transmissions from the reader interfere, but the reader users algorithm(s) to select the appropriate signal. | Reader transmissions are separated, i.e., reader guard bands prevent collisions. This protocol is an enhancement of the protocol of the Class 1 radio frequency identification tag. |

The major differences between the Class 0 and the Class 1 radio frequency identification tags are twofold. The first is that the Class 0 radio frequency identification tag has been defined by EPCglobal as a read-only device. A number is placed on a radio frequency identification tag, the number can be read, but it cannot be modified. The Class 1 radio frequency identification tag has been defined in the EPCglobal specification as a radio frequency identification tag that is one-time programmable. In other words, the radio frequency identification tag starts off as blank, the EPC is encoded, and that code can never be changed again. In practice, the originator of the Class 1 radio frequency identification tag now has radio frequency identification tags that are re-programmable, and the originator of the Class 0 radio frequency identification tag has a radio frequency identification tag that is fully re-writeable. However, the Class 0 radio frequency identification tags and the Class 1 radio frequency identification tags did not provide the data functionality nor did they meet geographic RF emission requirements across the world. Accordingly, the Class 1 Generation 2 radio frequency identification tags will be designed to support the 96-bit EPC code and have the provision for extra data to be carried in the radio frequency identification tag based on a single radio frequency identification protocol. Although the Class 0, the Class 1, and the Class 1 Generation 2 radio frequency identification tags are now available, it is expected that radio frequency identification tags that use high frequency radio waves and that are in compliance with the Class 1 Generation 2 radio frequency identification tags will become the dominant type of radio frequency identification tag on packaging. There is still support in the standards for the Class 0 and the Class 1 radio frequency identification tags, which support is likely to continue into the future so long as these radio frequency identification tags continue to constitute a large proportion of the technology in use. It should also be noted that at least four other classes of radio frequency identification tags exist, namely, Class 2, Class 3, Class 4, and Class 5 radio frequency identification tags, which are described in CHAUDHRY, N., THOMPSON, D., and THOMPSON, C., RFID Technical Tutorial and Threat Modeling Version 1.0 [online], Dec. 8, 2005 [retrieved on Jun. 9, 2008]. Retrieved from the Internet: <URL: http://www.csce.uark.edu/~drt/presentations/rfid-tutorial-threats-051201.pdf>, incorporated herein by reference.

Radio frequency identification technology has been contemplated for improving the configuration control of medical instruments and the supply chain visibility of components, assemblies, and sub-assemblies of medical instruments. Currently, information relating to the identity of the components, the assemblies, and the sub-assemblies of medical instruments and the maintenance and replacement of these components, assemblies, and sub-assemblies are recorded manually, and the repairs and replacements are recorded in writing. This procedure can lead to transcription errors and missing or inaccurate information. The manually recorded information is not readily accessible or traceable, and is not in a form that can be communicated to those who need to know the status regarding the configurations of the numerous medical instruments in assorted locations over a wide geographical area.

SUMMARY OF THE INVENTION

In one aspect of this invention, this invention provides a system for the tracking of medical instruments, such as, for example, automated diagnostic analyzers, components thereof, assemblies thereof, and sub-assemblies thereof, and maintenance information relating to the foregoing. According to the system, radio frequency identification tags are attached to or affixed on the medical instrument itself for the purpose of locating, identifying, monitoring, tracking the medical instrument and updating the maintenance and replacement activities relating to the medical instrument. In addition, radio frequency identification tags are attached to or affixed on the components, the assemblies, and the sub-assemblies of the medical instrument in order to locate, identify, monitor, track the components, the assemblies, and the sub-assemblies, and update the maintenance and replacement activities relating to these components, assemblies, and sub-assemblies.

The system comprises:
  (a) at least one medical instrument having a plurality of components, assemblies, sub-assemblies, or combinations of the foregoing, at least one of said plurality of components, assemblies, sub-assemblies, or combinations of the foregoing having a radio frequency identification tag affixed thereto;
  (b) a master radio frequency identification tag affixed to said medical instrument;
  (c) a first client/server, said first client/server comprising at least one of a database server and a file server.

The medical instrument can be any automated diagnostic analyzer, such as, for example, a clinical chemistry analyzer or an immunoassay analyzer. The medical instrument itself can have a radio frequency identification tag; each major component, assembly, or sub-assembly of the medical instrument can have a radio frequency identification tag; each minor component, assembly, or sub-assembly of the medical instrument can have a radio frequency identification tag on the container in which it is packaged. A master radio frequency identification tag correlated with a database is employed in order to collect information relating to all of the radio frequency identification tags associated with the medical instrument.

The system for tracking of medical instruments, alternately referred to herein as a configuration management system, comprises an optional world-wide call management system (alternately referred to as "WWCMS"), an optional communications module, such as, for example, a Wi-Fi device, a cellular telephone, a satellite transceiver, or a combination of the foregoing, and, optionally, a receiver of the Global Positioning System. By augmenting the configuration management system with the Global Positioning System (GPS) and a Wi-Fi device, a cellular telephone, a satellite transceiver, or combination of the foregoing, the system described herein enables the entity that manages the system to access configuration information remotely and further enables the entity that manages the system to track the location(s) of the medical instruments(s) in the system.

In another aspect, this invention provides a method for operating the system previously described. This method comprises the steps of:
  (a) placing a radio frequency identification tag on a component, an assembly, or a sub-assembly if the component, the assembly, or the sub-assembly is large enough to have a radio frequency identification tag attached thereto or a package containing a component, an assembly, or a sub-assembly if the component, the assembly, or the sub-assembly is too small to attach a radio frequency identification tag thereto;
  (b) loading the number of the component, the assembly, or the sub-assembly onto the radio frequency identification tag;
  (c) loading the serial number of the medical instrument onto the radio frequency identification tag;
  (d) updating the master radio frequency identification tag; and
  (e) uploading data from the master radio frequency identification tag to a database.

Any of or all of step (a), step (b), or step (c) can be performed by the manufacturer or supplier of the component, the assembly, or the sub-assembly, or by a field service engineer.

In still another aspect, this invention provides the ability for the entity that manages the system to have remote access to the configuration management system by means of the Global Positioning System.

The configuration management system described herein and the method for employing it provides the following capabilities:
  (a) ability to automate configuration identification during manufacturing of a medical instrument;
  (b) ability to provide supply chain visibility for the components, the assemblies, and the sub-assemblies of the medical instrument;
  (c) ability to automate configuration tracking during service and support of the medical instrument;
  (d) ability to capture custom modifications during service and support of the medical instrument;
  (e) ability to centralize system configuration information for the purpose of compliance and for the purpose of asset management relating to the medical instrument and the components, the assemblies, and the sub-assemblies thereof.

DETAILED DESCRIPTION

As used herein, the acronym "FSE" means field service engineer. A field service engineer is an individual who has been trained to repair and maintain automated analyzers at the customer's location. As used herein, the acronym "FRU" means field replaceable unit. A field replaceable unit is a component that can be quickly and easily removed from a piece of equipment and replaced by the user or by a technician without having to send the entire piece of equipment to a repair facility. As used herein, the acronym "TSB" means technical service bulletin. A technical service bulletin is a document that provides information to a technician relating to a particular procedure for performing service on an analyzer or component thereof. Technical service bulletins are recommended procedures for repairing equipment. Not to be confused with recalls, a TSB is issued by a manufacturer when there are several occurrences of an unanticipated problem. While sometimes written by engineers employed by original equipment manufacturers, the majority are written by the first technician to develop a procedure for repairing the equipment. As used herein, the acronym "ECN" means engineering change notice. An engineering change notice is a document which records or authorizes a change to design. The reasons for the change should also be recorded.

As used herein, the expression "radio frequency identification" means an automatic identification technology whereby digital data encoded in a radio frequency identification tag is capture by a reader using radio waves. As used herein, the expression "master radio frequency identification tag" means a radio frequency identification tag that can be used to collect information from a plurality of radio frequency identification tags relating to one medical instrument, such as, for example an automated clinical analyzer, comprising a plurality of components, assemblies, and sub-assemblies. In this specification, the expression "radio frequency identification tag" means a radio identification tag used for an individual component, an individual assembly of components, an individual sub-assembly of components, or the individual medical instrument itself, and does not include the master radio frequency identification tag.

As used herein, the expression "memory location" means a section of the memory on the microchip of a radio frequency identification tag. Each section of a memory can be read individually, i.e., without reading the other sections of the memory, or can be written to individually, i.e., without writing to the other sections of the memory. Some sections of the memory might be locked, so data cannot be overwritten, while others are not.

As used herein, the term "microchip" means a miniaturized electronic circuit that has been manufactured on the surface of a thin substrate of semiconductor material. Radio frequency identification tags comprise at least one microchip. As used herein, the term "antenna", when referring to a radio frequency identification tag, means the conductive element of the tag that enables the tag to send and receive data. Passive, low frequency (135 kHz), and high frequency (13.56 MHz) tags usually have a coiled antenna that couples with the coiled antenna of the reader to form a magnetic field. Ultra-high frequency tag antennas can have a variety of shapes. As used herein, the term "transmitter" means an electronic device for launching an electromagnetic wave or delivering an electromagnetic field for the purpose of transmitting or communicating energy or modulated data or information. The transmitter is often considered separately from the antenna, as the means whereby the antenna is energized. In this respect, the transmitter is also referred to as an exciter. As used herein, the term "transponder" means an electronic TRANSmitter/resPONDER, commonly referred to as a tag. As used herein, the term "transceiver" means a TRANSmitter/reCEIVER device to both receive and transmit data. As used herein, the term "reader", frequently referred to as an "interrogator", is an electronic device for performing the process of retrieving data from a transponder and, as appropriate, the contention and error control management, and channel and source decoding required to recover and communicate the data entered at the source. The device may also interface with an integral display and/or provide a parallel or serial communications interface to a host computer or industrial controller. A reader also has an antenna, which is used to emit radio waves. The radio frequency energy from the reader antenna is "harvested" by the tag antenna and used to power up the microchip, which then changes the electrical load on the antenna to reflect back its own signals.

As used herein, the term "Class 0" refers to one of the protocols defined by EPCglobal for exchanging information between a radio frequency identification tag and a reader for radio frequency identification tags. As used herein, the term "Class 1" refers to another of the protocols defined by EPCglobal for exchanging information between a radio frequency identification tag and a reader for radio frequency identification tags. Class 0 radio frequency identification tags and Class 1 radio frequency identification tags are further described in ID TECHNOLOGY, WHAT IS RFID & HOW WILL IT IMPACT MY BUSINESS? [online], [retrieved on Jun. 9, 2008]. Retrieved from the Internet: <URL: http://www.idtechnology.com/images/whitepapers/idtechnology-what-is-rfid.pdf>, incorporated herein by reference. As used herein, the term "Class 1 Generation 2" refers to still another of the protocols defined by EPCglobal for exchanging information between a radio frequency identification tag and a reader for radio frequency identification tags. Approved by EPCglobal in December 2004, the Class 1 Generation 2 air interface protocol provides a number of enhancements that will help solidify the adoption of radio frequency identification in the UHF band. Class 1 Generation 2 establishes a single UHF specification, where previously there were several, including EPC Class 1, EPC Class 0, and two from ISO.

See Alien Technology, EPCglobal Class 1 Gen 2 RFID Specification. White Paper [online], 2005 [retrieved on Jun. 11, 2008]. Retrieved from the Internet: <URL: http://www.alientechnology.com/docs/AT_wp_EPCGlobal_WEB.pdf>, incorporated herein by reference. Another reference that is useful for understanding radio frequency identification technology is CHAUDHRY, N., THOMPSON, D., and THOMPSON, C., RFID Technical Tutorial and threat Modeling Version 1.0 [online], Dec. 8, 2005 [retrieved on Jun. 9, 2008]. Retrieved from the Internet: <URL: http://www.cs-ce.uark.edu/~drt/presentations/rfid-tutorial-threats-051201.pdf>, incorporated herein by reference.

As used herein, the term "configuration" means the relative positioning or arrangement of the components, the assemblies, and the sub-assemblies of a medical instrument. As used herein, the expression "configuration tracking" means monitoring the changes in the configuration of components, assemblies, and sub-assemblies in a medical instrument. As used herein, the expression "configuration management" means the handling or control of the relative positioning or arranging of the components, the assemblies, and the sub-assemblies of a medical instrument. Configuration management is discussed in CROW, K., CONFIGURATION MANAGEMENT AND ENGINEERING CHANGE CONTROL [online], DRM Associates, 2002 [retrieved on Jun. 4, 2008]. Retrieved from the Internet: <URL: http://www.npd-solutions.com/configmgt.html>, incorporated herein by reference.

As used herein, the term "database" means a structured collection of records or data that is stored in a computer system and relies on software to organize the storage of that data. As used herein, the term "loading", "uploading", and the like, means the transfer of electronic information or data between at least two computers, systems, or media, such as radio frequency identification tags.

As used herein, the expression "medical instrument" means a clinical analyzer, such as, for example, an automated clinical analyzer, e.g., an automated immunoassay analyzer. As used herein, the term "component" means an individual part of a mechanical or electrical system. As used herein, the term "assembly" means a set of parts combined to make a completed product. As used herein, the term "sub-assembly" means a subdivision of an assembly that is designed to operate with other sub-assemblies in a manufactured product.

As used herein, the term "system" means a functionally related group of elements, such as, for example, a group of interacting mechanical and/or electrical components. As used herein, the term "server" means a computer system in a network that is shared by a multiplicity of users. The term "server" can refer to both the hardware and the software (the entire computer system) or just the software that performs the service. As used herein, the expression "file server" means a high-speed computer in a network that stores the programs and data files shared by the users. As used herein, the expression "database server" means a server that holds the database management system and the databases. Upon requests from the client machines, the database server searches the database for selected records and passes them back over the network. A database server and a file server may be one and the same, because a file server often provides database services. However, the expression "database server" implies that the system is dedicated for database use only and not a central storage facility for applications and files. As used herein, the expression "application server" means a server that runs the programs and processes the data. Before the Web, the expression referred to a computer in a client/server environment that performed the business logic (the data processing). In a two-tier client/server environment, which is most common, the user's machine performs the business logic as well as the user interface, and the server provides the database processing. In a three-tier environment, a separate computer (application server) performs the business logic, although some part may still be handled by the user's machine. In the Web environment, application servers became Web-based. As used herein, the expression "client/server" means an architecture in which a user's personal computer (the client) is the requesting machine and the server is the supplying machine, both of which are connected via a local area network or wide area network. Additional details relating to the types of server described herein can be found at the following Internet locations:

ChannelWeb: Tools and information for the solution provider community. [online], [retrieved on Jun. 11, 2008]. Retrieved from the Internet: <URL: http://www.crn.com/encyclopedia/shared/printerFriendlySrc.jhtml?term=client/server>; ChannelWeb: Tools and information for the solution provider community. [online], [retrieved on Jun. 11, 2008]. Retrieved from the Internet: <URL: http://www.crn.com/encyclopedia/shared/printerFriendlySrc.jhtml?term=file server>; ChannelWeb: Tools and information for the solution provider community. [online], [retrieved on Jun. 11, 2008]. Retrieved from the Internet: <URL: http://www.crn.com/encyclopedia/shared/printerFriendlySrc.jhtml?term=databaseserver>; ChannelWeb: Tools and information for the solution provider community. [online], [retrieved on Jun. 11, 2008]. Retrieved from the Internet: <URL: http://www.crn.com/encyclopedia/shared/printerFriendlySrc.jhtml?term=application server>; all of which are incorporated herein by reference.

As used herein, the term "interface" means a physical or electrical interconnection between communicating devices.

As used herein, the expression "air interface" means the conductor free medium, usually air, between a transponder and a reader/interrogator through which data communication is achieved by means of a modulated inductive or propagated electromagnetic field.

As used herein, the acronym "GPS" means Global Positioning System. The Global Positioning System was developed for and managed by the United States military. GPS is a satellite navigation system. GPS consists of 24 satellites above the earth. The satellites transmit radio signals to receivers placed on ships, trucks, or other large assets that need to be tracked. The receivers compute longitude and latitude and velocity by calculating the difference in time signals that are received from four different satellites. Some companies are integrating radio frequency identification and GPS systems to track assets in transit.

As used herein, the term "Wi-Fi" means a trade name for a popular wireless technology used in home networks, mobile phones, video games, and more. Wi-Fi is supported by nearly every modern personal computer operating system and most advanced game consoles. The purpose of Wi-Fi is to hide complexity by enabling wireless access to applications and data, media, and streams. The main aims of Wi-Fi are to facilitate access to information, ensure compatibility and coexistence, eliminate cabling and wiring, and eliminate switches, adapters, plugs, and connectors. The term "Wi-Fi" is a contraction of wireless fidelity and is meant to be used generically when referring to any type of 802.11 network, whether 802.11b. 802.11a, dual-band, etc. Any products tested and approved as "Wi-Fi Certified" by the Wi-Fi Alliance are certified as interoperable with each other, even if they are from different manufacturers. A user with a "Wi-Fi Certified" product can use any brand of access point with any other brand of client hardware that also is certified. Typically, however, any Wi-Fi product using the same radio frequency (for example, 2.4 GHz for 802.11b or 11g, 5 GHz for 802.11a) will work with any other, even if not "Wi-Fi Certified." 802.11 and 802.11x, where "x" represents a suffix letter, e.g., a, b, refers to a family of specifications developed by the IEEE for wireless LAN technology. 802.11 specifies an over-the-air interface between a wireless client and a base station or between two wireless clients. Additional discussion of Wi-Fi can be found at the following Internet locations:

Wi-Fi—Wikipedia, the free encyclopedia [online], [retrieved on Jun. 4, 2008]. Retrieved from the Internet: <URL: http://en.wikipedia.org/wiki/WiFi>; What is Wi-Fi?—A Word definition From the Webopedia Computer Dictionary [online], [retrieved on Jun. 10, 2008]. Retrieved from the Internet: <URL: http://www.webopedia.com/TERM/W/Wi_Fi.html>; What is 802.11—A Word definition From the Webopedia Computer Dictionary [online], [retrieved on Jun. 10, 2008]. Retrieved from the Internet: <URL: http://www.webopedia.com/TERM/8/802_11.html>; all of which are incorporated herein by reference.

As used herein, the trademark ECCOSORB® refers to a class of materials capable of absorbing radio frequency energy, which material can be used to reduce undesirable reflections from objects and devices and/or prevent signal loss to ground planes. ECCOSORB® materials are commercially available from Emerson & Cuming Microwave Products, Inc., 28 York Avenue, Randolph, Mass. 02368.

The symbol "(s)" following the name of an object indicates that either the object alone or a plurality of the objects is being referred to, depending upon the context of the statement surrounding the mention of the object or objects.

Additional discussion of radio frequency identification technology, including definitions of various terms and expressions, can be found in Radio Frequency Identification (RFID). White Paper [online]. Accenture, 2001 [retrieved on May 23, 2008]. Retrieved from the Internet: <URL: http://www.accenture.com/NR/rdonlyres/D27DDAE-9-CAB2-43B5-B6F2-27BD4F22EC1C10/rfidwhitepaperenov01.pdf>; Frequently Asked Questions About RFID Technology. Brochure [online]. Zebra Technologies, 2004 [retrieved on May 23, 2008]. Retrieved from the Internet: <URL: http://www.zebra.com/id/zebra/na/en/index/rfid/faqs.html>; and Technologies: RFID/RFID Glossary. Brochure [online]. Association for Automatic Identification and Mobility [retrieved on May 23, 2008]. Retrieved from the Internet: <URL: http:/www.aimglobal.org/technologies/rfid/rfid. Glossary.asp>, all of which are incorporated herein by reference.

Radio frequency identification tags are a key feature of the configuration management system, or configuration tracking system, described herein. Because data can be added to or deleted from radio frequency identification tags, radio frequency identification tags are much more flexible than bar codes, which cannot be modified once printed. Furthermore, unlike bar codes, radio frequency identification tags can accumulate and store historical facts pertaining to a component of a medical instrument. Any memory location or any group of memory locations on a radio frequency identification tag can be written to without disturbing the contents of the other locations. Each radio frequency identification tag can be assigned a serial number. The serial number of the radio frequency identification tag can serve to differentiate a plurality of components, assemblies, and sub-assemblies contained within or placed adjacent to a single medical instrument. For example, if a given instrument has three pipette assemblies, each of the pipette assemblies can be assigned a different serial number. Each of the plurality of pipette assemblies can have the serial number of the medical instrument added to the radio frequency identification tag of the assembly to complete the information necessary for configuration management at the assembly level.

Figure 1:
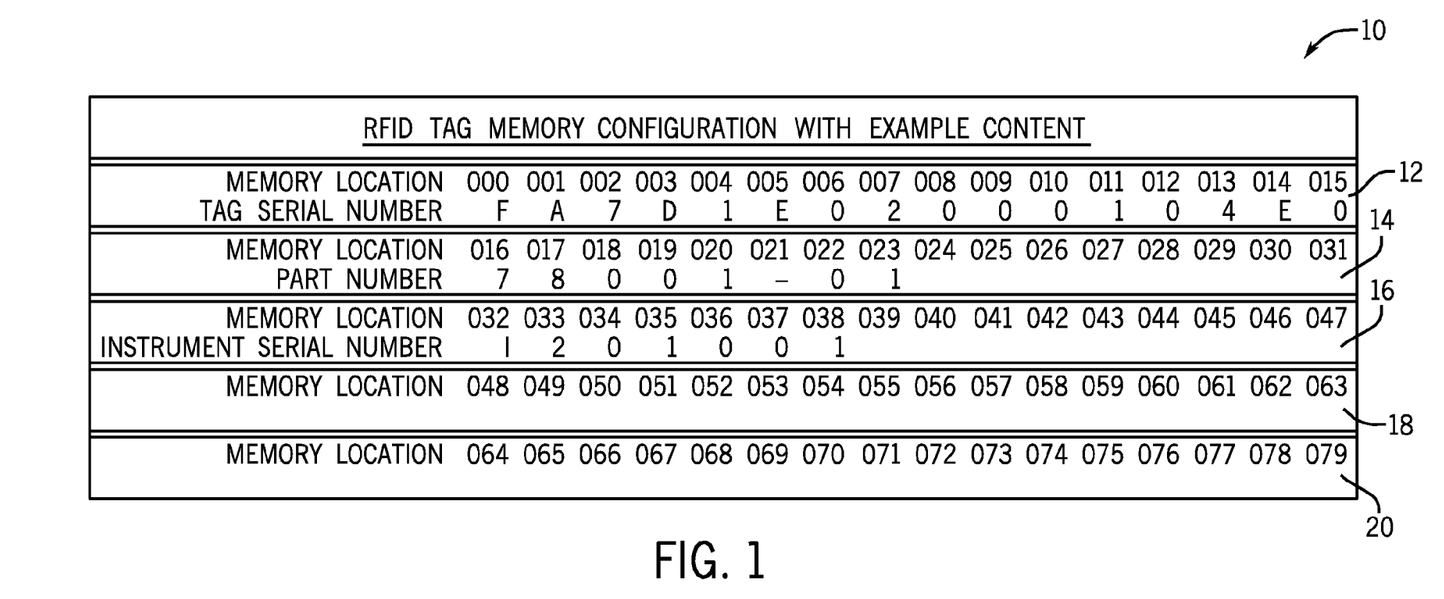
FIG. 1 is a diagram illustrating data contained in a radio frequency identification tag, which shows the memory location of the serial number of the tag, the memory location of the number of a component of a medical instrument, the memory location of the serial number of a medical instrument, and the memory location for data relating to the updating of the configuration of a medical instrument.

FIG. 1 is a schematic diagram showing certain types of data 10 that can be contained in a radio frequency identification tag. The type of radio frequency identification tag contemplated for containing the data shown in FIG. 1 is assigned to a particular component, assembly, or sub-assembly of a medical instrument. The data 10 contained in the radio frequency identification tag includes a serial number of the radio frequency identification tag in a first memory location 12. The data 10 contained in the radio frequency identification tag includes a component number in a second memory location 14. The data 10 contained in the radio frequency identification tag includes a serial number of a medical instrument in a third memory location 16. The radio frequency identification tag can include additional memory location(s) 18, 20 for storing data relating to updating of the configuration of a medical instrument.

The data contained on the radio frequency identification tags of the various components, assemblies, and sub-assemblies of the medical instrument can be collected on a master radio frequency identification tag. Then, the master radio frequency identification tag can be read directly, or can be accessed at a remote location, to provide a list of the components, the assemblies, and the sub-assemblies of the medical instrument, thereby enabling the data relating to the configuration of the medical instrument to be uploaded to a centralized database. Such configuration management enables the manufacturer or distributor of the medical instrument to recall components, assemblies, or sub-assemblies of the medical instrument if a manufacturing defect is discovered. In addition, such configuration management enables data mining, which facilitates the development of software programs to enable the determination of excessive wear of a component of a medical instrument, whereby the time of expected failure can be predicted. The master radio frequency identification tag can be supplied when the medical instrument is manufactured, and the master radio frequency identification tag can be maintained by field service engineers. An example of configuration flow of a sub-assembly implemented by means of radio frequency identification tags is illustrated in FIGS. 2 and 3.

Figure 2:
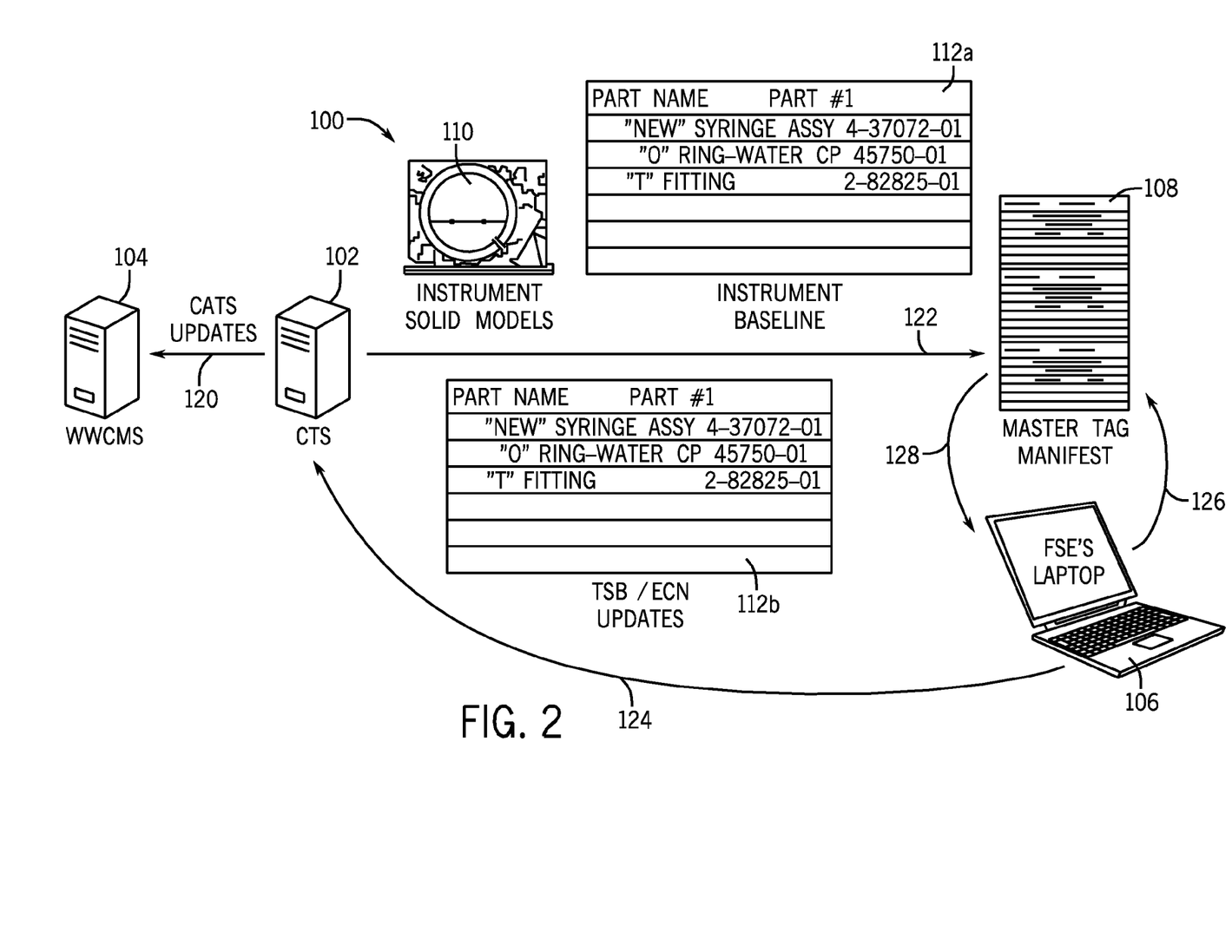
FIG. 2 is a schematic diagram illustrating the types of components that can be included in the system described herein. The components include a world-wide call management system, a configuration tracking system, and a master radio frequency identification tag. The medical instrument is not shown, but a medical instrument is needed as the object upon which the system operates. A portable computer for use by a field service engineer is also shown, but the portable computer is separable from the system.
Figure 3:
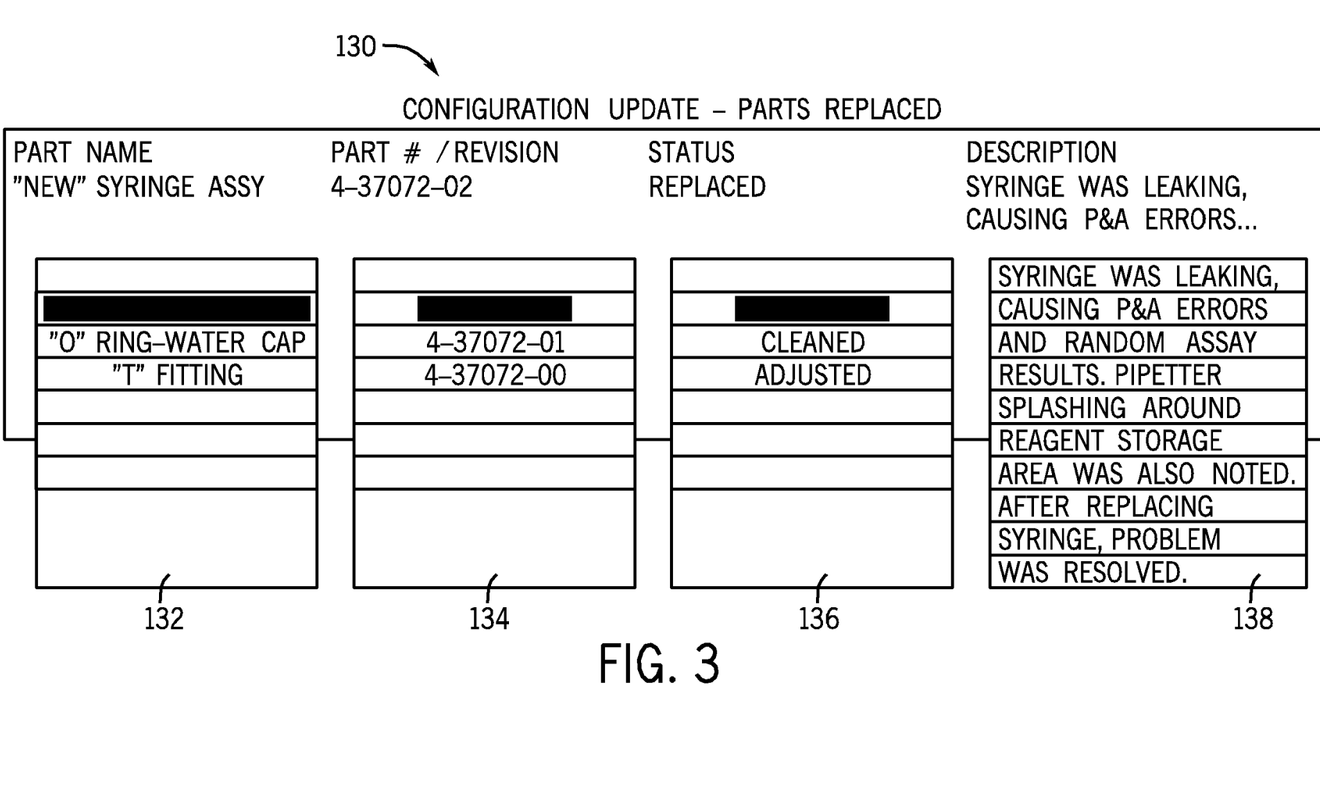
FIG. 3 is a schematic diagram illustrating the updating of a master radio frequency identification tag resulting from the replacement of an assembly of a medical instrument.

FIG. 2 shows a schematic diagram of a configuration management system 100 comprising:

(a) a client/server 102 that represents the central database of the configuration management system;

(b) a client/server 104 that represents a world-wide call management system; and (c) a portable computer 106 for entering data to update a master radio frequency identification tag.

It should also be noted that a field service engineer can use the portable computer 106 to update the individual radio frequency identification tag of a component, an assembly, or a sub-assembly, when the field service engineer performs a service on the component, the assembly, or the sub-assembly, such as, for example, cleaning, adjusting, modifying the component, the assembly, or the sub-assembly.

The client/server 102 typically comprises at least one of a database server and a file server. The client/server 104 also typically comprises at least one of a database server and a file server. The client/server 102 can also include an application server. Similarly, the client/server 104 can also include an application server.

FIG. 2 shows certain types of data 108 contained in the master frequency identification tag. Also shown in FIG. 2 is a visual model 110 of a medical instrument, which can be used to identify components, assemblies, or sub-assemblies of a medical instrument (not shown) that are required to be replaced, either on account of failure or preventive maintenance. This use of a visual model eliminates errors resulting from translation from one language to another, e.g., from English to German. The visual model can be viewed on the monitor of the portable computer. A controllable approach, e.g., a touch-screen having areas specified for various functions or operations, or a "point-and-click" approach, e.g., a mouse, can be used to assure the integrity of the data and reduce the effort on the part of the field service engineer (FSE) to correctly identify and provide documentation for the components, the assemblies, or the sub-assemblies replaced. It should be noted that FIG. 2 does not actually show the actual medical instrument, but the medical instrument must be present in order to replace or service components, assemblies, or sub-assemblies and to update the master radio frequency identification tag. Also shown in FIG. 2 is a portion 112*a* of the data 108 of the master radio frequency identification tag, which shows the baseline status of a syringe assembly of the medical instrument. The expression "baseline status" means the status of the syringe assembly of the medical instrument prior to a repair, replacement, or other change to the syringe assembly. Also shown in FIG. 2 is a portion 112*b* of the data 108 of the master radio frequency identification tag, which shows the updated status of the same syringe assembly that was the subject of the data 108 in portion 112*a*. The expression "updated status" means the status of the syringe assembly of the medical instrument subsequent to the repair, replacement, or other change to the syringe assembly by a field service engineer in response to a technical service bulletin, an engineering change notice, or some other type of request or demand for a repair, a replacement, or another change to the syringe assembly.

In the system shown in FIG. 2, each component, assembly, or sub-assembly of the medical instrument can have a radio frequency identification tag attached thereto when the component, the assembly, or the sub-assembly is delivered to the customer. If the component, the assembly, or the sub-assembly is too small, the radio frequency identification tag is attached to the package containing the component, the assembly, or the sub-assembly. This radio frequency identification tag can contain supply chain information, such as, for example, the commercial source of the component, the assembly, or the sub-assembly. This radio frequency identification tag can also be used to track the component, the assembly, or the sub-assembly throughout the manufacturing process. It is also preferred that this radio frequency identification tag be capable of being updated with date of delivery and the serial number of the medical instrument on which the component, the assembly, or the sub-assembly is installed. Each radio frequency identification tag contains data relating to the name of the component, the assembly, or the sub-assembly associated with the radio frequency identification tag, the identification number of the component, the assembly, or the sub-assembly associated with the radio frequency identification tag, the status of replacement, if any, of the component, the assembly, or the sub-assembly associated with the radio frequency identification tag, and the description, if any, of a service operation relating to the component, the assembly, or the sub-assembly associated with the radio frequency identification tag.

In the system shown in FIG. 2, the data 108 contained in the master radio frequency identification tag includes the data contained by each radio frequency identification tag of each component, assembly, or sub-assembly of the medical instrument with which a radio frequency identification tag is associated.

In order to comply with various industrial standards, such as, for example, FDA standards and international standards such as ISO, identification and tracking of components, assemblies, and sub-assemblies of the medical instrument during the manufacturing process may be required. Such tracking typically includes the identification of the commercial source of a component, an assembly, or a sub-assembly. Radio frequency identification systems enable the automation of the configuration process during manufacturing and also provide information relating to the source of components, assemblies, and sub-assemblies of a medical instrument.

After a medical instrument has been built and tested, a manifest of components, assemblies, and sub-assemblies of the medical instrument and procedures used to build and test the medical instrument can be programmed into the master radio frequency identification tag of the medical instrument. The master radio frequency identification tag is a radio frequency identification tag that is typically attached to the frame of the medical instrument. The master radio frequency identification tag is approximately the size of a conventional credit card, is operated by a battery, and interfaces with a communication device, such as, for example, a cellular transceiver, a satellite transceiver, a Wi-Fi transceiver. The data 108 contained in the master radio frequency identification tag includes the data 10 contained by each individual radio frequency identification tag associated with the medical instrument. In FIG. 2, the data 108 contained in the master radio frequency identification tag includes data for three syringe assemblies, because the subject medical instrument contains three syringe assemblies. Representative examples of master radio frequency identification tags that are commercially available, include, but are not limited to radio frequency identification tags that are commercially available from sources such as, for example, Texas Instruments, Philips Semiconductors, Motorola. A representative example of a master radio frequency identification tag suitable for use with the configuration management system (configuration tracking system) described herein is the MIFARE MF1ICS50 radio frequency identification tag, commercially available from NXP, a company founded by Philips. This master radio frequency identification tag is described in detail in the product data sheet entitled MF1ICS50 Functional specification, Rev. 5.3-29 Jan. 2008, Document identifier: 001053, NXP B.V., pages 1-19, incorporated herein by reference. Additional data can be added to the master radio frequency identification tag of the system when deemed appropriate. Such data can include, but is not limited to, data related to location of the medical instrument, data related to shipping of the medical instrument, etc.

After the medical instrument is installed at the site of a customer, and after each service call subsequent to the initial installation, any additional components, assemblies, and sub-assemblies of the medical instrument provided or replaced, procedures performed on the medical instrument or on the components, the assemblies, or the sub-assemblies thereof, or modifications made to the medical instrument or on the components, the assemblies, or the sub-assemblies thereof, can be documented by means of the master radio frequency identification tag, and the contents of the updated master radio frequency identification tag can be either copied to a central database, i.e., which is located at a home base or at a command headquarters, or connected to a Wi-Fi device, cellular telephone, or satellite transceiver by means of an interface to enable a remote user to obtain access to this documentation. In addition, this remote access capability can be connected with the receiver of the Global Positioning System by means of an interface so that the exact location of an installed medical instrument can be determined.

FIG. 2 shows several connections between various components of the configuration management system 100. The arrow 120 between the client/server 102 and the client/server 104 represents a step for updating a complaint activity tracking system. The purpose of the complaint activity tracking system is to manage activities of the field service engineers and activities related to complaints of customers. A complaint activity tracking system is one aspect of customer relationship management, which is an information industry term for methodologies, software, and usually Internet capabilities that help an enterprise manage customer relationships in an organized way. For example, an enterprise might build a database about its customers that describes relationships in sufficient detail so that managers, salespersons, persons providing service, and perhaps the customer directly could access information, match needs of customers with plans for products and offerings for products, remind customers of service requirements, know what other products a customer had purchased, and so forth. The implementation of the configuration management system (or configuration tracking system) described herein along with the complaint activity tracking system allows the formation of individualized relationships with customers, with the aim of improving customer satisfaction and optimizing profits, identifying problems of customers, and providing customers the a high level of service. The configuration management system (or configuration tracking system) also provides the enterprise and the field service engineers with the information and processes necessary to assist the customers, understand and identify needs of the customers, and effectively build relationships between the enterprise, its customer base, and distribution partners. Software for the area of customer relationship management is commercially available from sources such as, for example, Oracle Corporation, SAP AG, Siebel Systems, Inc.

The arrow 122 between the client/server 102 and the master radio frequency identification tag 108 indicates that the master radio frequency identification tag is initially constructed along with the medical instrument by means of the visual models and the baseline of the medical instrument, i.e., the list of components, assemblies, and sub-assemblies of the medical instrument. The arrow 124 between the field service engineer's portable computer 106 and the client/server 102 represents the communication from the portable computer 106 to the client/server 102, whereby the updated configuration of the medical instrument, resulting from repair or replacement of a component, an assembly, or a sub-assembly is communicated to the client/server 102. The arrow 126 between the field service engineer's portable computer 106 and the master radio frequency identification tag 108 represents the configuration of the medical instrument prior to repair or replacement of a component, an assembly, or a sub-assembly of the medical instrument. The arrow 128 between the master radio frequency identification tag 108 and the field service engineer's portable computer 106 represents the configuration of the medical instrument subsequent to repair or replacement of a component, an assembly, or a sub-assembly of the medical instrument.

FIG. 3 shows a set of electronic data input forms that are completed by a field service engineer when a configuration of a medical instrument is updated. For the purpose of exemplification, the configuration is updated by replacing at least one syringe assembly. The collection of electronic data input forms 130 indicates the operation of replacing a syringe assembly. An electronic data input form 132 indicates the name of the component, the assembly, or the sub-assembly being replaced, i.e., a syringe assembly. An electronic data input form 134 indicates the number of the component, the assembly, or the sub-assembly being replaced, e.g., a syringe assembly, and the revision number, e.g., 4-37072-02. An electronic data input form 136 indicates the status of the component, the assembly, or the sub-assembly replaced, e.g., replaced, cleaned, and adjusted. An electronic data input form 138 indicates the description of the problem, if any, and the nature of the correction of the problem, e.g., leaking, precision and accuracy error, random assay results. In electronic data input forms 132, 134, 136, and 138, a prompt appears on the monitor of the portable computer 106 indicating to the field service engineer the information that is to be entered in order to capture changes in the configuration of the medical instrument and other cleaning, adjusting, and other maintenance procedures performed on the medical instrument. The actual operation of entering the information is of a difficulty approximately equivalent to that of making a routine airline reservation by means of a website on the internet. However, the field service engineer has a relatively high degree of discretion in describing the nature of the problem(s) addressed and any observations relating to the problem(s) addressed. In order for a field service engineer to update a radio frequency identification tag for a component, an assembly, a sub-assembly, or a medical instrument itself, the radio frequency identification tag must be capable of being read and written to. A representative example of a radio frequency identification tag that is capable of being read and written to is a Class 1 Generation 2 radio frequency identification tag. Similarly, in order for a field service engineer to update a master radio frequency identification tag for a medical instrument, the master radio frequency identification tag must be capable of being read and written to. A representative example of a master radio frequency identification tag that is capable of being read and written to is a Class 1 Generation 2 radio frequency identification tag. In general, the radio frequency identification tag of a component, an assembly, or a sub-assembly of a medical instrument, or of the medical instrument itself, is not written to unless a custom modification is made by a field service engineer in the field or unless a custom service is performed by a field service engineer in the field.

Figure 4:
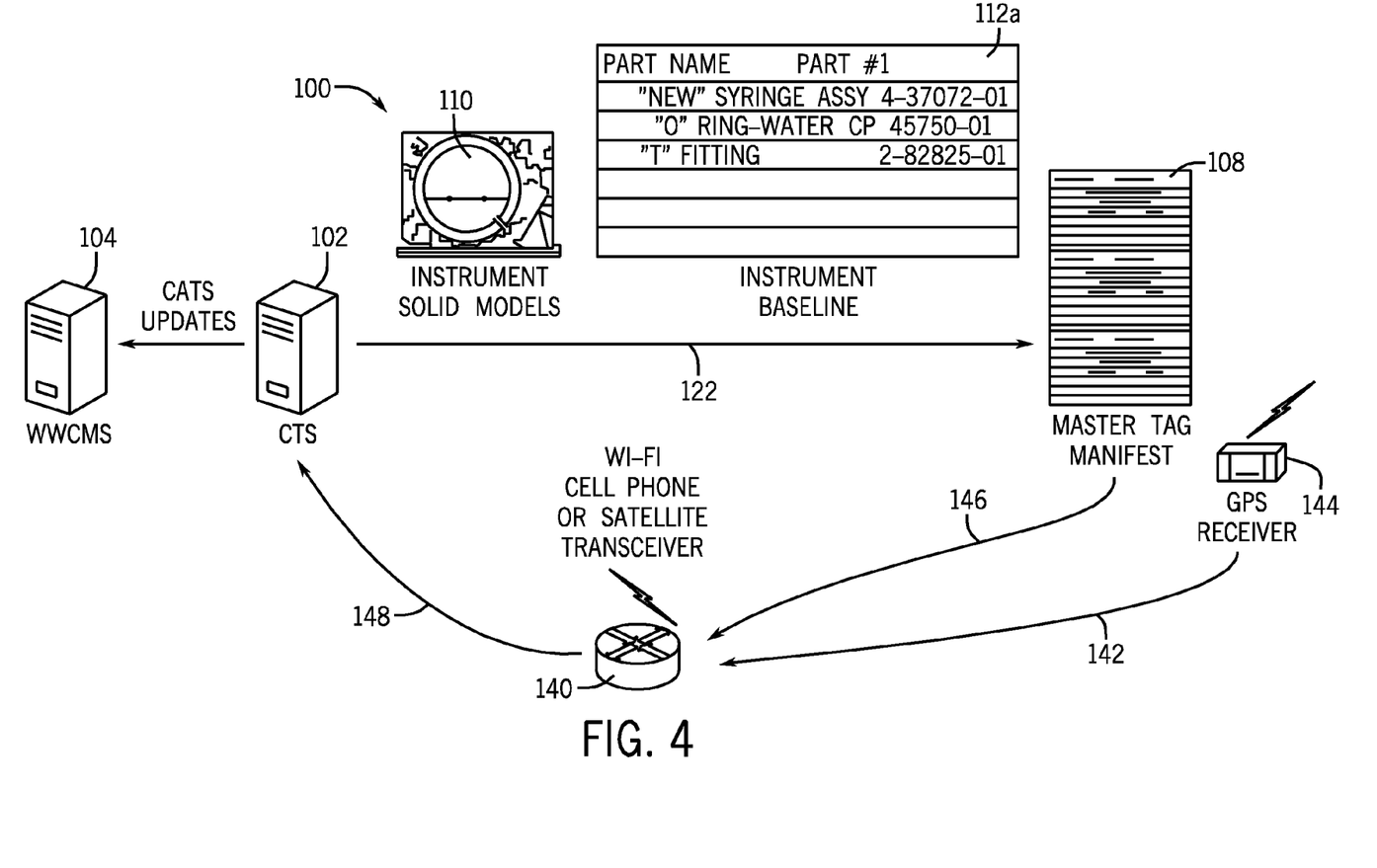
FIG. 4 is a schematic diagram illustrating a remote communication arrangement for the system shown in FIG. 2.

FIG. 4 shows how the system communicates with various communication devices in order to transmit the data resulting from a configuration update to the central database. In addition to showing the client/server 102, the client/server 104, and the data 108 contained in the master radio frequency identification tag as were shown in FIG. 2, FIG. 4 shows how the master radio frequency identification tag can communicate with a communications module 140, such as, for example, a Wi-Fi device, a cellular telephone, or a satellite transceiver. Alternatively, a non-wireless connector, such as, for example, a USB port, can be used. See for example, RFID Journal—RFID (Radio Frequency Identification) Technology News & Features, Orbit One Launches Satellite-Based RFID Service. News article. [online], [retrieved on Jun. 10, 2008]. Retrieved from the Internet: <URL: http://www.rfid-journal.com/article/article view/3896/1/1/>, incorporated herein by reference. FIG. 4 also illustrates a connection 142 between the communications module 140, e.g., a Wi-Fi device, a cellular telephone, or a satellite transceiver and the receiver of the Global Positioning System 144. FIG. 4 also illustrates a connection 146 between the data 108 contained in the master radio frequency identification tag and the communications module 140 and a connection 148 between the communications module 140 and the client/server 102.

Service technicians (field service engineers) need access to information relating to the configurations of medical instruments when they are in the field, i.e., remote from the home base or command headquarters. Configuration management systems help to automate the process of collecting such information, with the result that a central database can store information relating to the actual configuration of the medical instruments in the field, thereby allowing better management of inventory to enable timely shipping of components, assemblies, and sub-assemblies for the purpose of repair or replacement of defective, worn, damaged, or obsolete components, assemblies, and sub-assemblies of a medical instrument.

In the event of a recall of a particular component, assembly, or sub-assembly, or a field wide service action, such as, for example, the recall of a defective valve for a probe washing mechanism, the exact configuration of each medical instrument, and the location of each medical instrument, can be determined, thereby allowing more efficient management of inventory and assets. Shipping of components, assemblies, and sub-assemblies for the purpose of repair or shipping of components, assemblies, and sub-assemblies for the purpose of replacement, or service routing, i.e., providing the exact location to which a component, an assembly, or a sub-assembly is to be sent, can be scheduled and performed more quickly and at reduced cost.

When medical instruments are moved to different hospitals, laboratories, locations, etc., information related to such movement is not always recorded. Implementing a remote access system with the Global Positioning System can enable knowledge of geographical location of a medical instrument, even when the instrument is moved from an initial geographical location to a subsequent geographic location.

Figure 5:
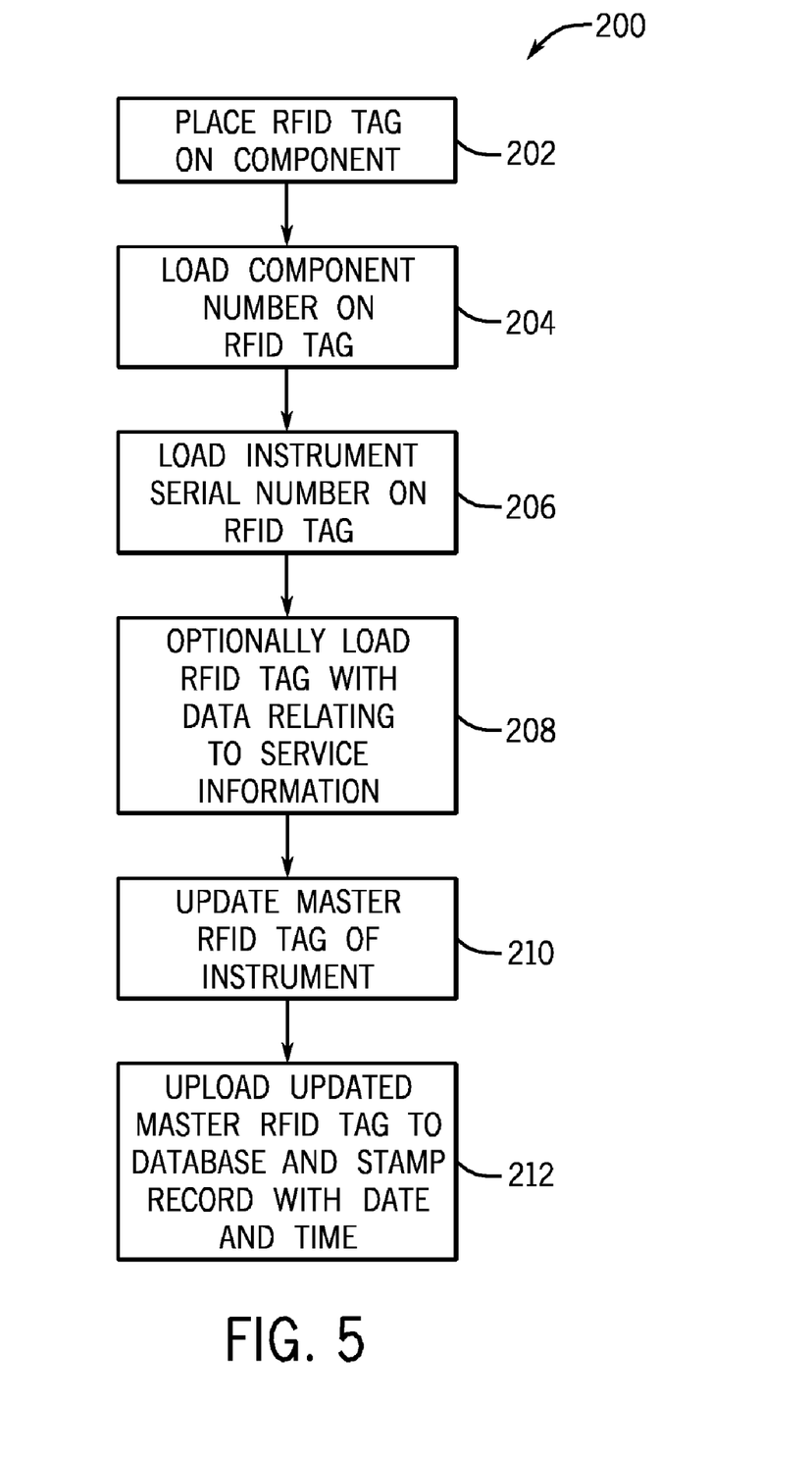
FIG. 5 is a flow chart illustrating a process for operating the system embodied in FIGS. 1, 2, 3, and 4.

FIG. 5 shows a method for recording the history of data placed on master radio frequency identification tags. This method 200 comprises the steps of:
(a) serializing, i.e., assigning a serial number to, a radio frequency identification tag (step 202);
(b) loading the radio frequency identification tag with the number of a component, an assembly, or a sub-assembly of a medical instrument, or the medical instrument itself, the medical instrument having a master radio frequency identification tag (204);
(c) loading the serial number of the medical instrument to the radio frequency identification tag (206);
(d) optionally loading the radio frequency identification tag with data relating to cleaning, adjusting, or other maintenance information (208)
(e) updating the master radio frequency identification tag of the medical instrument with the data from the radio frequency identification tag of the component, the assembly, or the sub-assembly (210);
(f) uploading the master radio frequency identification tag to the database (212).

The information in the radio frequency identification tags can be protected (from reading and writing) by means of commercially available encryption techniques to prevent proprietary information from being captured or altered in an unauthorized manner.

The system described herein provides the ability to record supply chain data, i.e., the commercial source of a component, an assembly, or a sub-assembly, for each component, assembly, or sub-assembly of a medical instrument. Radio frequency identification tags can contain many times more information than can bar codes (e.g., over 100 times more). The system described herein further provides the ability to automate the checking of information relating to configuration of any components, assemblies, or sub-assemblies in a medical instrument and store this information in a master radio frequency identification tag of the medical instrument. The system described herein still further provides the ability to document modifications made by a field service engineer in the field to a component, an assembly, or a sub-assembly of the medical instrument and to the medical instrument itself. The system described herein also has the ability to provide an interface to a master radio frequency identification tag to enable access to the configuration of the medical instrument from a location remote from the medical instrument.

The radio frequency identification tags described herein can also be programmed with special information relating to updates or special information relating to service in order to monitor and account for defects that would mandate a recall or replacement of a component, an assembly, or a sub-assembly of a medical instrument and to verify that a field service engineer has carried out maintenance actions required by or suggested by the manufacturer or supplier of the medical instrument. Radio frequency identification technology enables the automation of tracking the configuration of the components, the assemblies, and the sub-assemblies during service and technical support procedures. For example, the master radio frequency identification tag can be updated with a manifest of all the information on the radio frequency identification tags of all the components, the assemblies, and the sub-assemblies in order to provide a record of all changes made to the medical instrument, as shown in FIGS. 3 and 5.

The aforementioned description provides the basis for the following example of testing. The system and the subsequent testing thereof were primarily based on a medical diagnostic analyzer (ARCHITECT® i2000, commercially available from Abbott Laboratories), but the method can be adapted to any complex system having a plurality of medical instruments, each medical instrument having a plurality of components, assemblies, and sub-assemblies.

The system described herein employs radio frequency identification technology to improve the management of the configuration of a system for any type of medical instrument or types of medical instruments. For demonstration purposes, the radio frequency identification tags used were high frequency (13.56 MHz) and in compliance with ISO14443.

As field replaceable units are replaced, the configuration of the master radio frequency identification tag is updated and the data of the master radio frequency identification tag is synchronized with the data of the portable computer of the field service engineer.

The following non-limiting example further describes the system previously described.

Example

The following equipment was used to demonstrate the operation of the configuration management system described herein:
Medical Instrument:
ARCHITECT® i2000 immunoassay analyzer was used. (De-energized, i.e., not plugged into an electrical outlet and having its cover in place)

Reader:

Escort Memory Systems LRP7400 Reader/Writer (13.56 MHz) was used.

Radio Frequency Identification Tags:

ExypnoTech 13.56 MHz radio frequency identification tags were used. The radio frequency identification tags were in compliance with ISO15693, Philips I-code protocol. The radio frequency identification tags were Class 1 radio frequency identification tags Master Radio Frequency Identification Tag:

EMS (Escort Memory Systems) radio frequency identification tag was used. The master radio frequency identification tag was not used in this example.

Shielding:

ECCOSORB® material BSR-1/SS-6M of 0.010 inch thickness was used when the radio frequency identification tag was placed on a metal portion of a component, an assembly, or a sub-assembly.

Components, Assemblies, Sub-Assemblies:

Group 1: components, assemblies, and sub-assemblies that can be tagged and read successfully outside the instrument. Examples of these components, assemblies, and sub-assemblies include, but are not limited to, (a) MPC860 CPU printed circuit board assembly, (b) liquid level sense circuit board, (c) bar code reader for reagent containers, (d) Architect system control center CPU, and (e) controller board for solenoid DC motor.

Group 2: components, assemblies, and sub-assemblies that are too small to tag and would be tagged on their packaging. Examples of these components, assemblies, and sub-assemblies include, but are not limited to, (a) O-rings, (b) microswitch, (c) V-wheels (6-pack), (d) valve for syringe, (e) thermistor for clot detecting assembly, and (f) reaction vessel transport reaction vessel detector.

Group 3: components, assemblies, and sub-assemblies that can be tagged and can be read in place in the instrument, i.e., the radio frequency identification tag can be read without the need to open the medical instrument. Examples of these components, assemblies, and sub-assemblies include, but are not limited to, (a) reaction vessel loader, (b) reaction vessel load diverter, (c) load queue bar code reader for sample identification, (d) process queue bar code reader assembly, and (e) vacuum accumulator assembly.

Group 4: components, assemblies, and sub-assemblies that can be tagged and require ECCOSORB® material to be readable, such as, for example, when metal surfaces interfere with the radio frequency identification tag. Examples of these components, assemblies, and sub-assemblies include, but are not limited to, (a) reagent refrigeration unit, (b) syringe, (c) vortexer for process path, (d) motor for optics shutter, and (e) pump for automated reconstitution module.

Group 5: components, assemblies, and sub-assemblies that can be tagged and can be read in place in the instrument using ECCOSORB® material, i.e., the radio frequency identification tag can be read without the need to open the medical instrument. Examples of these components, assemblies, and sub-assemblies include, but are not limited to, (a) theta-Z pipettor assembly, (b) process path drive motor, (c) wash zone diverter assembly, (d) reaction vessel unloader diverter assembly, and (e) process path.

The difference between the items in Group 4 and Group 5 is that the radio frequency identification tags in Group 5 can be read without the need to open the medical instrument.

Group 6: components, assemblies, and sub-assemblies that are not listed in the database containing a listing of Field Replaceable Units (FRU). Examples of these components, assemblies, and sub-assemblies include, but are not limited to, (a) harness cable #7, (b) kit for access door for the process queue, (c) left internal cover, (d) reservoir buffer, and (e) reaction vessel access door.

The ARCHITECT® i2000 immunoassay analyzer was selected to test the application of the configuration management system employing the radio frequency identification technology described herein. A total of 108 components, assemblies, and sub-assemblies were identified, based on one year's worth of worldwide service data. The components, the assemblies, and the sub-assemblies selected constituted 72% of the total number of components, assemblies, and sub-assemblies replaced and the costs of the components, the assemblies, and the sub-assemblies selected constituted 90% of the cost for replacement components, assemblies, and sub-assemblies for the ARCHITECT® i2000 immunoassay analyzer. Where possible, radio frequency identification tags were affixed to components, assemblies, and sub-assemblies positioned in the ARCHITECT® i2000 immunoassay analyzer. Components, assemblies, and sub-assemblies that were too small for direct attachment of radio frequency identification tags thereto would have radio frequency identification tags affixed to the exterior of the packages containing these components, assemblies, and sub-assemblies. The radio frequency identification tag of each component, assembly, or sub-assembly was read where the radio frequency identification tag was accessible, e.g., affixed to a component, an assembly, or a sub-assembly or on a container for the component, the assembly, or the sub-assembly. Components, assemblies, and sub-assemblies that contained a relatively high percentage of metallic material, such as, for example, a pipettor frame, which is typically formed from aluminum, were fitted with a layer of ECCOSORB® BSR-1/SS-6M of 0.010 inch thickness to prevent the radio frequency identification signal from being absorbed by and not reflected by the sub-assembly. The layer of ECCOSORB® BSR-1/SS-6M of 0.010 inch thickness was applied in such a manner as to be between the reader and the component, the assembly, or the sub-assembly. The test exercise of the ARCHITECT® i2000 immunoassay analyzer is summarized in TABLE 2.

TABLE 2

| Group | Number | Tag positioned on item | Tag positioned on package | Tag read in medical instrument | Tag requires ECCOSORB® layer |
|---|---|---|---|---|---|
| 1 | 57 | Yes | | | |
| 2 | 20 | | Yes | | |
| 3 | 11 | Yes | | Yes | |
| 4 | 8 | Yes | | | Yes |
| 5 | 7 | Yes | | Yes | Yes |
| 6 | 5 | | | | |
| Total | 108 | | | | |

The test results confirm that the radio frequency identification technology described herein is capable of supporting a configuration management system wherein radio frequency identification tags are read and written to. As shown in TABLE 2, the radio frequency identification tag can be affixed to components, assemblies, and sub-assemblies themselves or to the packaging thereof. However, the memory space of the radio frequency identification tag must be sufficient to provide the key elements in the chain of configuration control. As used herein, the expression "key elements" means the number of a component, assembly, or sub-assembly; the number of a medical instrument; the changes effected; the updates effected. It should be noted that in this EXAMPLE, only the ability to read a radio frequency identification tag was tested.

The invention described herein allows the identity of the manufacturer, the entities in the supply chain, the serial number of the component, the assembly, or the sub-assembly, any revision number, the chain of custody, to be attached via a radio frequency identification tag to a component, an assembly, or a sub-assembly or to the medical instrument itself. These radio frequency identification tags can be read from a distance of up to about one foot, preferably from a distance of less than about six inches, by means of a radio frequency identification reader. A distance of less than about six inches is preferred so that the readers read only one radio frequency identification tag at any given time. The complete configuration of the system can be identified or verified (i.e., read) or both prior to the date and time that the medical instrument leaves the factory, or anytime after a service procedure has been performed.

Augmenting the radio frequency identification technology described herein with a cellular telephone or Wi-Fi transceiver allows configuration information to be accessed remotely, provided that the cellular telephone Wi-Fi transceiver resides in a geographic location that is serviced by the provider of the communication system. Optionally, a satellite telephone transceiver can be used anywhere in the world, but this implementation is currently excessively costly. Implementing the configuration management system employing the radio frequency identification technology described herein and cellular technology with a receiver of the Global Positioning System allows a location to be added to the data that pertains to the configuration of the system. As noted previously, radio frequency identification tags can be protected by means of commercially available encryption techniques to prevent tampering with or capture of proprietary information.

Radio frequency identification technology helps to automate the configuration process during service and support procedures. Master radio frequency identification tags can be updated with a complete list of components, assemblies, and sub-assemblies and procedures contained in the medical instrument. Such automation would prevent mistakes when manually transcribing information on TSB stickers.

Radio frequency identification allows specified field modifications to be documented on parts and/or systems. This process cannot be supported by "read only" bar codes.

Various modifications and alterations of this invention will become apparent to those skilled in the art without departing from the scope and spirit of this invention, and it should be understood that this invention is not to be unduly limited to the illustrative embodiments set forth herein.

What is claimed is:

1. A system for tracking the location of components, assemblies, and sub-assemblies in an automated diagnostic analyzer comprising:
   (a) at least one automated diagnostic analyzer having a plurality of components, assemblies, sub-assemblies, or combinations of the foregoing, at least one of said plurality of components, assemblies, sub-assemblies, or combinations of the foregoing having a radio frequency identification tag affixed thereto;
   (b) a master radio frequency identification tag affixed to the at least one automated diagnostic analyzer;
   (c) a first client/server, said first client/server comprising at least one of a database server and a file server.

2. The system of claim 1, wherein the radio frequency identification tag is capable of containing data relating to the name of the at least one component, assembly, or sub-assembly of the at least one automated diagnostic analyzer, the identification number of the at least one component, assembly, or sub-assembly of the at least one automated diagnostic analyzer, the status of repair or replacement, if any, of the at least one component, assembly, or sub-assembly of the at least one automated diagnostic analyzer, and the description, if any, of a service operation relating to the at least one component, assembly, or sub-assembly of the at least one automated diagnostic analyzer.

3. The system of claim 2, wherein the master radio frequency identification tag contains the data contained in by each radio frequency identification tag of each component, assembly, or sub-assembly of the at least one automated diagnostic analyzer having a radio frequency identification tag.

4. The system of claim 1, wherein the at least one automated diagnostic analyzer has a radio frequency identification tag affixed thereto.

5. The system of claim 1, wherein the at least one automated diagnostic analyzer is selected from the group consisting of clinical chemistry analyzers and immunoassay analyzers.

6. The system of claim 1, wherein at least one component, assembly, or sub-assembly of the at least one automated diagnostic analyzer has a radio frequency identification tag attached to a container in which said at least one component, assembly, or sub-assembly of the at least one automated diagnostic analyzer is packaged.

7. The system of claim 1, further including a second client/server, said second client/server comprising at least one of a database server and a file server.

8. The system of claim 7, wherein said second client/server further includes an applications server.

9. The system of claim 7, wherein said second client/server operates a world-wide call management system.

10. The system of claim 1, wherein said first client/server further includes an applications server.

11. The system of claim 1, wherein said system further includes a communications module.

12. The system of claim 11, wherein said communications module is selected from the group consisting of a Wi-Fi device, a cellular telephone, and a satellite transceiver.

13. The system of claim 11, further including a receiver of the Global Positioning System.

14. The system of claim 1, wherein said client of said first client/server comprises a portable computer.

15. A method for operating the system of claim 1, said method comprising the steps of:
   (a) placing a radio frequency identification tag on a component, an assembly, or a sub-assembly of the at least one automated diagnostic analyzer if the component, the assembly, or the sub-assembly of the at least one automated diagnostic analyzer is large enough to have a radio frequency identification tag attached thereto or a package containing a component, an assembly, or a sub-assembly of the at least one automated diagnostic analyzer if the component, the assembly, or the sub-assembly of the at least one automated diagnostic analyzer is too small to attach a radio frequency identification tag thereto;
   (b) loading the number of the component, the assembly, or the sub-assembly of the at least one automated diagnostic analyzer onto the radio frequency identification tag;
   (c) loading the serial number of the at least one automated diagnostic analyzer onto the radio frequency identification tag;
   (d) updating the master radio frequency identification tag; and (e) uploading data from the master radio frequency identification tag to a database.

16. The method of claim 15, wherein a portable computer carries out at least one of the steps of loading the number of the component, the assembly, or the sub-assembly of the at least one automated diagnostic analyzer onto the radio frequency identification tag, loading the serial number of the at least one automated diagnostic analyzer onto the radio frequency identification tag, updating the master radio frequency identification tag, and uploading data from the master radio frequency identification tag to a database.

17. The method of claim 16, wherein an electronic data input form is used to load the number of the component, the assembly, or the sub-assembly of the at least one automated diagnostic analyzer onto the radio frequency identification tag.

18. The method of claim 16, wherein an electronic data input form is used to load the serial number of the at least one automated diagnostic analyzer onto the radio frequency identification tag.

19. The method of claim 16, wherein an electronic data input form is used to update the master radio frequency identification tag.

20. The method of claim 16, wherein an electronic data input form is used to upload data from the master radio frequency identification tag to the database.

21. The method of claim 16, wherein an electronic data input form is used to load the number of the component, the assembly, or the sub-assembly of the at least one automated diagnostic analyzer onto the radio frequency identification tag.

22. The method of claim 16, wherein an electronic data input form is used to load the serial number of the at least one automated diagnostic analyzer onto the radio frequency identification tag.

23. The method of claim 16, wherein an electronic data input form is used to update the master radio frequency identification tag.

24. The method of claim 16, wherein an electronic data input form is used to upload data from the master radio frequency identification tag to a database.

25. The method of claim 15, wherein the master radio frequency identification tag communicates with a communications module.

26. The method of claim 25, wherein the communications module is a wireless communications module.

27. The method of claim 26, wherein the communications module is selected from the group consisting of a Wi-Fi device, a cellular telephone, and a satellite transceiver.

28. The method of claim 25, wherein the communications module is a non-wireless communications module.

29. The method of claim 25, wherein the communications module communicates with the Global Positioning System.

30. The method of claim 15, wherein a portable computer carries out at least one of the steps of loading the number of the component, the assembly, or the sub-assembly of the at least one automated diagnostic analyzer onto the radio frequency identification tag, loading the serial number of the medical instrument onto the radio frequency identification tag, updating the master radio frequency identification tag, and uploading data from the master radio frequency identification tag to a database.

31. A method for recording the history of data relating to the tracking of the configuration of an automated diagnostic analyzer, said data placed on a master radio frequency identification tag, said method comprising the steps of:
(a) serializing a radio frequency identification tag;
(b) loading the radio frequency identification tag with the number of a component, an assembly, or a sub-assembly of the automated diagnostic analyzer;
(c) adding the serial number of the automated diagnostic analyzer to the radio frequency identification tag;
(d) updating the master radio frequency identification tag of the automated diagnostic analyzer;
(e) uploading the master radio frequency identification tag to the database.

* * * * *